United States Patent [19]

Widlund et al.

[11] Patent Number: 5,391,162
[45] Date of Patent: Feb. 21, 1995

[54] SANITARY NAPKIN OR AN INCONTINENCE GUARD HAVING FLEXIBLE SIDE-FLAPS

[75] Inventors: Urban Widlund, Mölnlycke, Sweden; Helena Engqvist, Düsseldorf, Germany; Agneta Thorén, Landvetter, Sweden

[73] Assignee: Molnlycke AB, Goteborg, Sweden

[21] Appl. No.: 50,141

[22] PCT Filed: Oct. 31, 1991

[86] PCT No.: PCT/SE91/00735
§ 371 Date: Jul. 2, 1993
§ 102(e) Date: Jul. 2, 1993

[87] PCT Pub. No.: WO92/07536
PCT Pub. Date: May 14, 1992

[30] Foreign Application Priority Data

Nov. 1, 1990 [SE] Sweden ............... 9003490-1

[51] Int. Cl.6 .............................................. A61F 13/15
[52] U.S. Cl. .................... 604/385.2; 604/387
[58] Field of Search ................ 604/385.2, 373, 385.1, 604/387, 385

[56] References Cited

U.S. PATENT DOCUMENTS

| | | | |
|---|---|---|---|
| 4,608,047 | 8/1986 | Mattingly | 604/387 |
| 4,735,316 | 4/1988 | Froidh et al. | 206/438 |
| 4,808,177 | 2/1989 | DesMarais et al. | 604/385.1 |
| 5,062,839 | 11/1991 | Anderson | 604/385.1 |

FOREIGN PATENT DOCUMENTS

| | | |
|---|---|---|
| 0130848 | 1/1985 | European Pat. Off. |
| 0264952 | 4/1988 | European Pat. Off. |
| 0329160 | 8/1989 | European Pat. Off. |

Primary Examiner—Jerome L. Kruter
Attorney, Agent, or Firm—Young & Thompson

[57] ABSTRACT

An absorbent article such as a sanitary napkin or a guard for mildly incontinent persons, comprising an elongated absorbent pad (3) enclosed between a liquid-permeable casing sheet (1) facing the wearer in use of the article and a liquid-impermeable casing sheet (2). At least one of the casing sheets extends laterally beyond the absorbent pad forming an outwardly projecting, longitudinally extending edge. Flexible side-flaps (5, 6) are arranged at the long side edges of the absorbent pad (3) and are intended, when the article is used, to be folded around the edges of the wearer's underpants or like garment (9) in the crotch part thereof and attached to the outside of the underpants. Uplifted liquid barrier devices (10, 11) are provided on that side of the article which faces the wearer in use on both sides of the absorbent pad (3) along at least parts of the long side edges thereof between the absorbent pad and the flexible side-flaps. An end portion (12, 13) of each side-flap (5, 6) is attached to the corresponding outwardly projecting edge of the casing sheet(s) on that side thereof which, when the side-flaps are folded against the side of the article distal from the wearer in use, is facing away from the wearer. This end portion (12, 13) has an extent corresponding to the height desired for the respective liquid barrier device (10, 11).

9 Claims, 2 Drawing Sheets

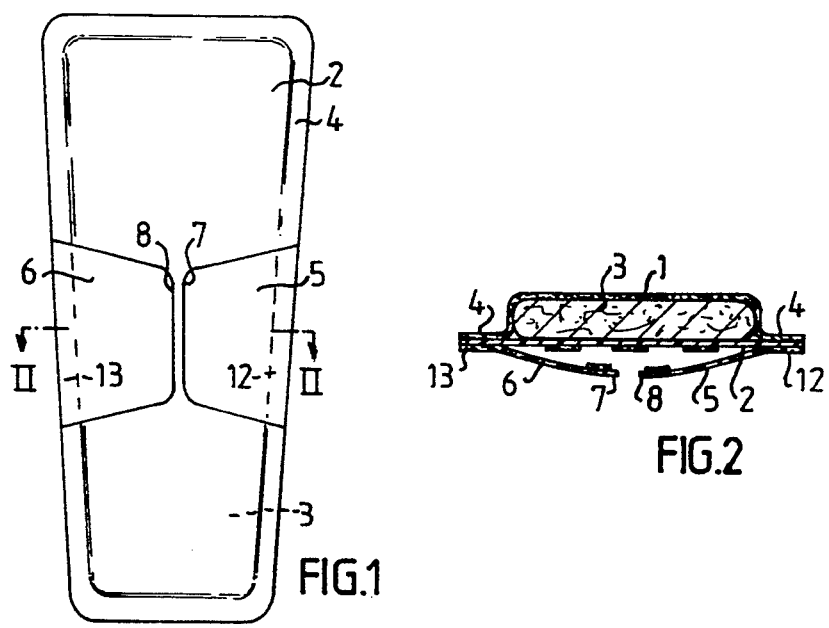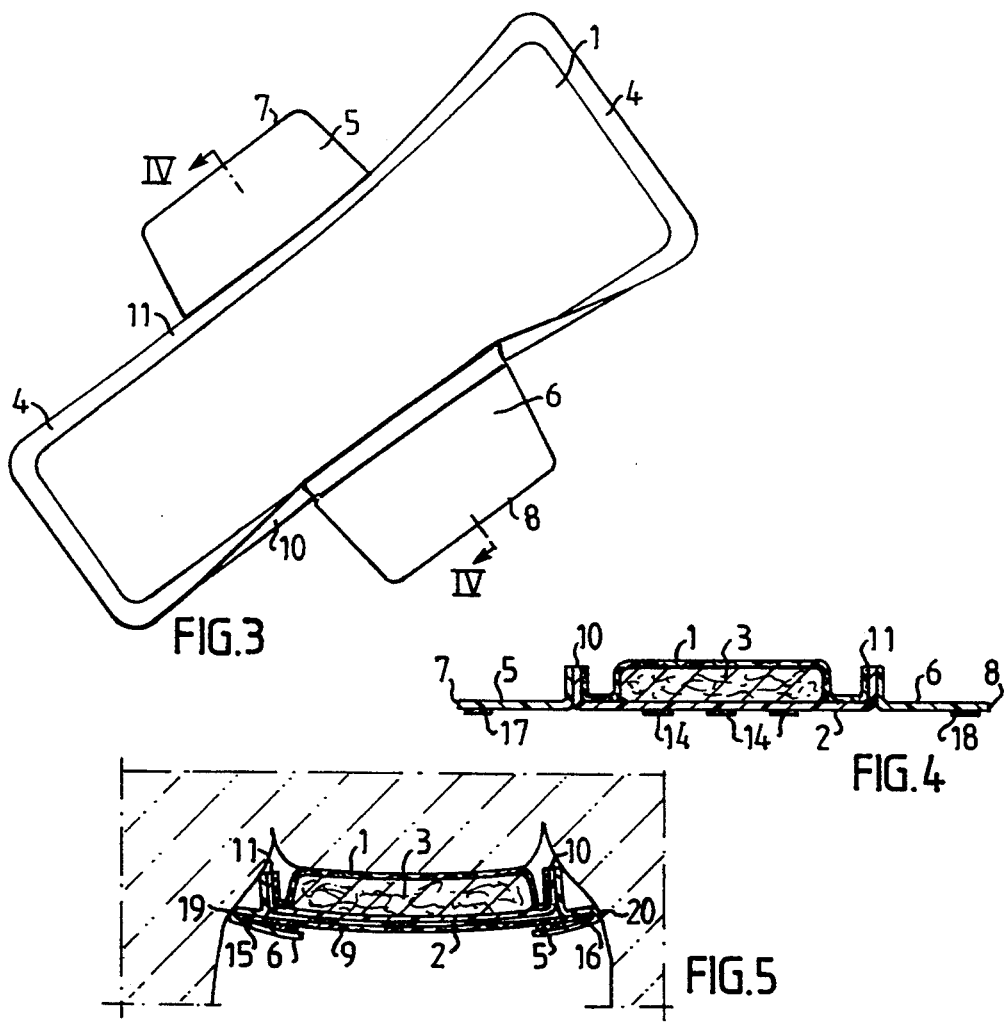

SANITARY NAPKIN OR AN INCONTINENCE GUARD HAVING FLEXIBLE SIDE-FLAPS

FIELD OF THE INVENTION

The present invention relates to an absorbent product, such as a sanitary napkin or an incontinence guard, which comprises an essentially elongated absorbent pad which is enclosed casing material, and flexible side-flaps which are disposed on the long side edges of the elongated absorbent pad and, when the article is worn, are intended to be folded around the crotch of the wearer's underpants or like garment and fastened to the outside of said pants.

BACKGROUND OF THE INVENTION

Articles of this kind are intended to be worn by menstruating women or by persons who suffer from relatively light incontinence, and who require the articles to afford protection against leakage but still be unnoticeable when worn beneath conventional clothing. Since the amount of fluid discharged with menstruation and with light incontinence is relatively small, the articles can be designed in a manner which enables them to be accommodated essentially completely in the crotch region of the wearer, between the wearer's thighs. The requirement that such articles shall be discrete when worn is satisfied almost to the full by said articles.

However, it has been found difficult to produce articles of this kind which are sufficiently proof against leakage. The main reason for this is that, when worn, the articles are highly deformed by the forces that are generated as the wearer moves. The greatest deformation normally occurs within that part of the article which, in use, is located in the narrowest space between the wearer's thighs. Unfortunately, this part of the article is also the part which is intended to receive the discharged body fluid first and to absorb said fluid. As a result of this pronounced deformation of the article, the surface area of the article available for direct absorption is, of course, greatly reduced. This increases the risk of body fluid leaking past the side edges of the article and soiling the user's underpants.

THE KNOWN PRIOR ART

A number of different solutions have been proposed with the intention of reducing the risk of this lateral leakage of body fluids. For example, SE 455 668, U.S. Pat. No. 4,285,343, EP 130 848, EP 134 086 and U.S. Pat. No. 4,608,047 teach methods of providing sanitary napkins with flexible side-flaps, or wings, which project outwardly from the absorbent pad. When fitting the article for wear, these side-flaps are intended to be folded around the edges of the leg openings of the wearer's underpants or like garment, and fastened to the outside thereof. The side-flaps form a guard against side-edge leakage and against soiling of the wearer's underpants. In addition, the side-flaps also, to some extent, counteract deformation of the absorbent pad, since the napkin is anchored to the leg edges of the underpants and is held stretched between the leg edges during use.

One serious drawback with the known so-called winged napkins, however, is that menstruation fluid often passes outside the absorbent pad and onto the flexible side-flaps. This can occur, for instance, when the napkin becomes wrinkled or folded, or when the napkin is positioned crookedly, such that menstruation fluid will pass outside the absorbent pad of the napkin from the very beginning and soils one of the side-flaps. Even though menstruation fluid has originally been absorbed by the absorbent pad, the fluid may be transported out to the side-flaps in the event of the absorbent pad becoming saturated with fluid, or should transverse fluid-conducting folds form in the absorbent pad during use.

Since the side-flaps are primarily intended to form liquid barriers, they seldom contain a large amount of absorbent material. Consequently, any liquid which reaches the side-flaps will be spread over a large area of the flaps. When this occurs, the known winged napkins become warm, dirty and unpleasant to wear, since they quickly obtain a large moist surface which lies in close contact with the wearer's body. Furthermore, there is a risk that liquid will spread past the side-flaps in the longitudinal direction of the napkin and leak onto the wearer's underpants. This risk increases, of course, with decreasing extensions of the side-flaps in the longitudinal direction of the napkin.

However, there are two main reasons why the side-flaps shall be as narrow as possible. Firstly, large side-flaps are too discernible on the outer surface of the wearer's underpants or like garment and are therefore not felt to be sufficiently discrete and, secondly, large side-flaps cannot be manipulated easily and are not readily folded around the curved leg edges of a pair of underpants.

When menstruation fluid reaches the side-flaps, or wings, of a sanitary napkin of this kind, instead of being absorbed by the absorbent pad, the used napkin becomes particularly unsightly, which is a further drawback. This naturally contributes still further to the sensation of wetness and discomfort when wearing the known winged sanitary napkins.

The present invention, however, provides an absorbent article of the aforedescribed kind which overcomes the drawbacks associated with earlier known winged sanitary napkins.

SUMMARY OF THE INVENTION

In accordance with the invention, the inventive article is mainly characterized by uplifted liquid barrier means disposed on that side of the article which will face towards the wearer in use, on both sides of the absorbent pad along at least parts of its long side edges, between the absorbent pad and the flexible side-flaps.

The uplifted edges provided along the absorbent pad will prevent body fluid from spreading into the flexible side-flaps.

This is partly because those folds or wrinkles which may form in the absorbent pad of said article in use, or in the casing sheet located nearest the wearer, are effectively cut-off by the uplifted liquid barriers. Such pleats or folds would otherwise cause the body fluid to spread out towards the edge parts of the article and into the flexible side-flaps.

The spreading of liquid to the side-flaps through the capillaries of the surface material of the article is also obstructed by means of the present invention, since the uplifted liquid barriers interrupt communication between the absorbent pad and the side-flaps of the article.

The uplifted liquid barrier devices can be obtained in various ways. For example, these devices may consist of uplifted folds in the napkin casing material which extend along the absorbent body. Such barrier devices can be produced readily and feel soft and comfortable to the wearer's skin. The uplifted folds may include liquid-impervious material, such as plastic film, or may be treated with a hydrophobic material, in order to further amplify the liquid barrier effect.

A conventional sanitary napkin and incontinence guard normally includes an absorbent pad which is enclosed between two casing layers or sheets. The edge parts of the respective casing sheets extend beyond the absorbent pad, around the periphery thereof, and are mutually joined within the confines of said outwardly projecting edge parts. According to the present invention, uplifted side edges are provided on this type of absorbent article by anchoring flexible side-flaps in the form of separate pieces of material to the outwardly projecting edge parts of the casing, on that side of the article which, in use, faces away from the wearer. In this case, it is important that the flexible side-flaps are only attached to those parts of the casing which project beyond the absorbent pad. The side-flaps shall also be attached in a manner such that their free ends face in towards the centre part of the article, since the side-flaps are not subjected to external influences. When the article is worn, the side-flaps are folded out from the absorbent pad. This will result in the formation of joins between the side-flaps and the uplifted edges of the casing edge parts on both sides of the absorbent pad, on that side of the article which faces towards the wearer in use. The flexible side-flaps thus serve to hold the liquid barrier devices of said article in an uplifted position during use. One advantage afforded by this particular embodiment of the invention is that relatively small side-flaps are also able to lift up the outwardly projecting casing parts along substantially the full length of the side edges of the absorbent pad. It is also possible to obtain effective barriers against edge leakage without needing to use large, not-readily manipulated and less-discrete side-flaps. The joins will preferably have essentially the same height or a smaller height than the absorbent pad, so as to avoid chaffing of the wearer's skin by the uplifted edge joins.

Another advantage afforded by this embodiment of the invention is that it is possible to choose freely the material from which the side-flaps are made, this choice being independent of the nature of the casing material of the article concerned. For example, it is not necessary for the side-flaps to be impervious to liquid, since there is practically no risk of liquid spreading to the side-flaps. It is, however, suitable to form the side-flaps from a material which is hydrophobic and which will resist wetting to a certain extent. The material used may also be a "breathable" material, so that air is able to pass through the material and onto the skin of the wearer, so that the article will feel dry and comfortable in use.

Uplifting of the liquid barrier devices against the body of the wearer can be facilitated by providing said devices with elastication. This elastication will also function to curve the article in its longitudinal direction, so that the article will fit against the wearer's body more snugly.

BRIEF DESCRIPTION OF THE DRAWINGS

The invention will now be described in more detail with reference to an exemplifying embodiment thereof and also with reference to the accompanying drawings.

FIG. 1 illustrates from above a sanitary napkin constructed in accordance with a first embodiment of the invention, said napkin being seen from the side which is remote from the wearer in use.

FIG. 2 is a sectional view of the sanitary napkin shown in FIG. 1, taken on the line II—II in said Figure.

FIG. 3 is a perspective view of the sanitary napkin shown in FIGS. 1 and 2, as seen from the side which faces towards the wearer in use.

FIG. 4 is a sectional view taken on the line IV—IV in FIG. 3.

FIG. 5 is a sectional view of the sanitary napkin shown in FIGS. 1-4 fitted within a pair of underpants, in use.

DETAILED DESCRIPTION OF THE PREFERRED EMBODIMENTS

Figure 6:
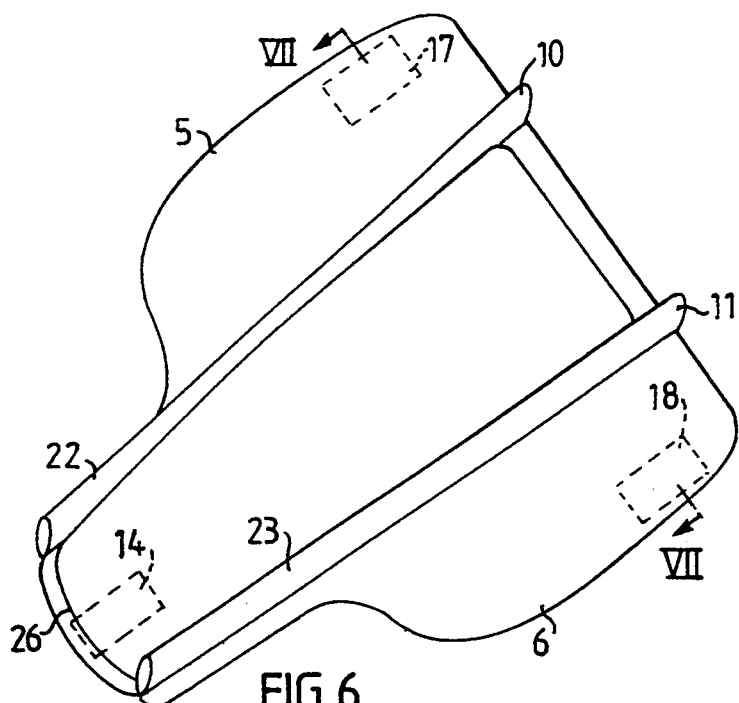
FIG. 6 is a perspective view of a second embodiment of an inventive sanitary napkin, seen from the side of the napkin which faces the wearer in use.

The sanitary napkin illustrated in FIGS. 1-5 includes a liquid-permeable casing layer I on that side of the napkin which faces towards the wearer in use. The liquid-permeable layer 1 is suitably made from a non-absorbent fabric or a perforated plastic film. The napkin also includes a liquid-impermeable casing layer 2, for example made of plastic film or a fabric, which has been made hydrophobic on that side of the napkin which is remote from the wearer in use. An absorbent pad 3 is enclosed between the two casing layers 1, 2. The absorbent pad 3 may comprise one or more layers of absorbent material, such as cellulose fluff, with or without being admixed with so-called superabsorbents. By superabsorbents is meant polymeric materials which are capable of absorbing liquid in quantities corresponding to many times their own weight. Superabsorbents are normally in the form of particles which are admixed with the cellulose fluff or which are applied in separate layers between adjacent fluff layers. Superabsorbents may also be in the form of flakes, granules, films and fibres as an alternative to particle form.

Although not shown in the drawings, the absorbent pad 3 may also include other features, such as a liquid dispersing layer and a reinforcing layer made, for instance, of tissue or fabric.

The two casing layers or sheets 1, 2 are slightly more expansive than the absorbent pad 3 and thus form an outwardly projecting edge 4 around the periphery of the absorbent pad 3. The casing sheets 1, 2 are joined together along the whole of the outwardly projecting edge 4, thereby encasing the absorbent pad 3 between the sheets 1, 2.

The sanitary napkin illustrated in FIGS. 1-5 also includes two soft and flexible side-flaps 5, 6, made for instance from fibre fabric, preferably a hydrophobic so-called spunbond material. The side-flaps 5, 6 are firmly anchored to the casing edges 4 projecting outwardly from the absorbent pad. This anchoring of the side-flaps and the mutual joining of the two casing sheets 1, 2 are preferably effected with the aid of known techniques, for example by gluing, heat-welding or ultrasonic-welding.

The side-flaps 5, 6 are attached to that side of the napkin which is remote from the wearer in use, with the free ends 7, 8 of the side-flaps 5, 6 facing inwardly towards the longitudinal centre line of the napkin. This enables the napkin to be readily manipulated for packaging purposes subsequent to manufacture. It is not necessary to fold the flexible side-flaps 5, 6 separately in order for the napkin to be given a suitable packaging configuration. This is a considerable advantage in comparison with earlier known sanitary napkins, with which the side-flaps 5, 6 project outwardly from the absorbent pad 3 subsequent to manufacture and must therefore be folded-in before the napkins can be packeted.

When a sanitary napkin constructed in accordance with the embodiment illustrated in FIGS. 1–5 shall be positioned within a pair of underpants, panties or like garment 9, in use, the side-flaps 5, 6 will project out from the absorbent 3, as shown in FIGS. 3 and 4. The side-flaps 5, 6 therewith force parts of the casing edge 4 projecting outwardly of the absorbent pad to rise, such as to form uplifted liquid barriers 10, 11 on both sides of the absorbent pad 3. The longitudinal extension of the liquid barriers 10, 11 will, of course, depend on the largeness of the casing edge 4 connected to respective side-flaps 5, 6. However, that part of the casing edge 4 which each side flap 5, 6 is able to lift is much greater than the actual joins 12, 13 between the side-flaps 5, 6 and the casing edge 4. This enables effective and efficient upwardly raised liquid barriers 10, 11 to be obtained even with relatively small side-flaps 5, 6. This is highly beneficial, particularly from the aspect of discretion and with view to the ease with which the napkin can be handled.

FIG. 5 is a section view which illustrates how the napkin is supported in the crotch region of the wearer. The napkin is secured to the underpants, panties, etc. 9 of the wearer by means of regions 14 of pressure-sensitive adhesive provided on the liquid-impermeable sheet 2 adjacent the end parts of the napkin. When fitting the napkin, the flexible side-flaps 5, 6 are folded around the edges 15, 16 of the leg openings of the underpants 9 and fastened to the outside of the underpants. Regions 17, 18 of pressure-sensitive adhesive are also provided on the side-flaps 5, 6 for the purpose of securing the napkin in position.

Because the absorbent pad 3 is slightly narrower than the crotch part of the underpants 9, the side-flaps 5, 6 will extend laterally from respective long edges of the absorbent pad, prior to folding the side-flaps 5, 6 around the edges 15, 16 of the leg openings of said underpants 9. During use, the elastications 19, 20 in the edges 15, 16 of said leg openings exert a given tensioning force on the napkin, such as to stretch the absorbent 3 and those parts of the side-flaps 5, 6 that are located between the edges 15, 16 of the leg openings in the transverse direction of the napkin. This tensioning force also holds the outwardly extending casing parts 10, 11 in a raised position along the long sides of the elongated absorbent pad 3. As before mentioned, these uplifted barriers 10, 11 are particularly effective against leakage of fluid past the edges of the napkin and against the spreading of liquid to the side-flaps 5, 6 of said napkin. Because the liquid-impermeable sheet 2 of the napkin extends out into the uplifted casing edges 10, 11, and because the side-flaps 5, 6 are made of separate pieces of material, there is no risk of liquid spreading over the liquid barriers 10, 11. As before mentioned, it is possible, and even appropriate, to produce the side-flaps 5, 6 from a liquid-permeable material. According to the inventive concept, the side-flaps 5, 6 are mainly intended to function as means for fitting an absorbent article 2 and for stretching said article in a pair of underpants or like garment and need not have liquid barrier properties. Thus, by producing the side-flaps from an air and moisture permeable material, it is possible to provide a sanitary napkin which is cooler and more comfortable than the earlier known sanitary napkins where the side-flaps formed a liquid-impermeable leakage barrier.

Figure 7:
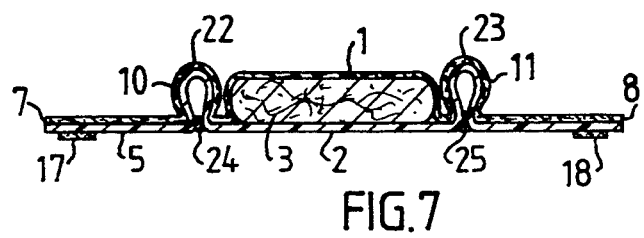
FIG. 7 is a sectional view of the napkin shown in FIG. 6, taken on the line VII—VII in said Figure.
Figure 8:
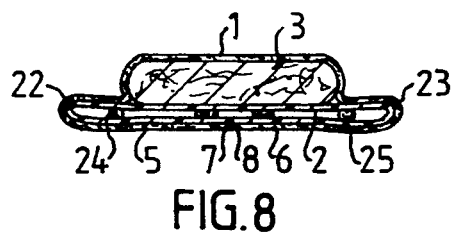
FIG. 8 illustrates the behaviour of the napkin shown in FIGS. 6 and 7 in use.

Similar to the sanitary napkin illustrated in FIGS. 1–5, the sanitary napkin illustrated in FIGS. 6, 7 and 8 includes a liquid-permeable casing sheet 1, a liquid-impermeable casing sheet 2, and an absorbent 3 encased between the two sheets 1, 2. The napkin also includes two side-flaps 5, 6 which are formed by parts of the casing sheets 1, 2 that extend beyond the longitudinal edges of the elongated pad 3. Similar to the embodiment aforedescribed, the free ends 7, 8 of the side-flaps 5, 6 are intended to be folded around and fastened to the crotch part of a pair of underpants or like garment 9, when the napkin is fitted for use. The side-flaps 5, 6 extend in the longitudinal direction of the napkin, from the forward edge 21 of the absorbent pad and rearwardly to a point that is located slightly beyond the transverse centre line of the napkin. The napkin also includes two longitudinally extending folds 22, 23, which are formed in the casing material between the longitudinal edges of the absorbent pad 3 and the side-flaps 5, 6. The folds 22, 23 are arranged on that side of the napkin which is intended to face the wearer in use, and extend on both sides of the pad 3 throughout the full length of the napkin. The folds 22, 23 are held joined by gluing said folds together on that underpants or the side of the binder which is distal from the wearer in use. This gluing of the folds 22, 23 is suitably effected with the aid of melt-glue beads 24, 25 provided along the whole length of the folds. Naturally, other types of adhesive can be used, or the folds can be welded together with the aid of neat or ultra-sonic welding techniques, for instance. If found suitable, the folds can be joined together over the whole of their widths.

Similar to the napkin illustrated in FIGS. 1–5, the napkin is secured to a pair of underpants or like garment 9, by means of regions of pressure-sensitive adhesive provided on the liquid-impermeable sheet 2. To this end, two adhesive regions 17, 18 are provided on the side-flaps 5, 6, close to the forward edge 21 of the napkin, and a further adhesive region 14 is provided on the rear end 26 of the napkin.

The side-flaps 5, 6 are preferably folded-in onto the liquid-impermeable sheet 2 subsequent to manufacture of the napkin, as illustrated in FIG. 8.

This will bring the napkin to a form suitable for packaging and transporting purposes, with the longitudinally extending folds 22, 23 folded down so as to project generally straight out from the long edges of the absorbent pad 3, in the same plane as the liquid-impermeable sheet 2. When the napkin is to be used, the side-flaps 5, 6 are unfolded, as shown in FIGS. 6 and 7. As the side-flaps are unfolded, the longitudinally extending folds 22, 23 will be forcibly raised such as to form liquid barriers 10, 11 on both sides of the absorbent pad 3. The napkin is then placed in a pair of underpants or like garment 9, in the same manner as the napkin of the embodiment illustrated in FIGS. 1–5, with the side-flaps 5, 6 folded securely around the crotch part of the underpants 9.

Because the liquid barriers 10, 11 are formed by folds 22, 23 in the napkin casing material 1, 2, those surfaces of the liquid barriers which lie against the wearer's body in use will be soft and rounded. This eliminates the risk of discomfort caused by chaffing of the wearer's skin.

Despite the fact that the liquid barriers 10, 11 extend along the full length of the napkin, whereas the side-flaps 5, 6 terminate immediately behind the transverse centre line of the napkin, the folds 22, 23 will be lifted along the whole of their lengths when the side-flaps 5, 6 are unfolded.

Figure 9:
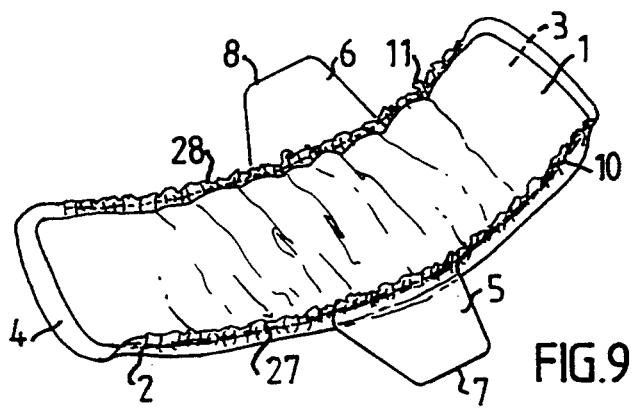
FIG. 9, finally, is a perspective view of a third embodiment of the inventive sanitary napkin, seen from the side of the napkin which faces towards the wearer in use.

The sanitary napkin illustrated in FIG. 9 is constructed generally in the same manner as the sanitary napkin illustrated in FIGS. 1–5. Consequently, those elements of the FIG. 9 embodiment which correspond to elements of the embodiment illustrated in FIGS. 1–5 have been identified by the same reference signs. The sanitary napkin shown in FIG. 9, however, is also provided with elastic devices 27, 28 in the uplifted liquid barriers 10, 11 on both sides of the absorbent pad 3 of the napkin. The elastic devices 27, 28 draw the liquid barriers 10, 11 together and thereby assist the barriers in reaching a raised position and also maintain said barriers in their raised position during the use of the napkin. The elastic devices 27, 28 also cause the napkin to curve in its longitudinal direction, so that the napkin is well adapted to the contour of this part of the wearer's body. The elastic devices 27, 28 need not extend along the full length of the napkin. For example, it may suffice to elasticate solely the centre parts of the uplifted liquid barriers. Suitable elastic devices in this respect are, for instance, spun elastic threads, elastic bands, elastic melt glue, or elastic foamed material.

Although the invention has been described in the aforegoing with reference to sanitary napkins, it will be understood that the invention can be applied equally as well to incontinence guards.

The invention shall not therefore be considered restricted to the described and illustrated embodiments. For example, it is possible to very the shape of both the side-flaps and the absorbent pad of the article.

The uplifted liquid barriers can be obtained by forming a fold solely in the liquid-permeable sheet. In the case of this embodiment, however, the fold should include some form of liquid obstructing material, for instance a plastic strip, or should be treated with an agent which makes the material hydrophobic.

Furthermore, the article may be held in position in a pair of underpants or like garment by means other than those illustrated and described. For example, the article may be provided with a friction agent, a self-gripping tape, or may have pressure-sensitive adhesive applied in patterns different to those illustrated and described.

The outwardly projecting side-flaps may be made of any appropriate material whatsoever, which may be elastic, for instance.

Furthermore, the uplifted liquid barriers may be folded-in towards the absorbent pad of the article and fastened to the liquid-permeable casing material at the end-parts of the liquid barriers. This will ensure that the liquid barriers are held permanently raised while the article is in use, and that liquid-accommodating pockets are formed on both sides of the absorbent pad.

We claim:

1. In an absorbent article to be worn by a person, comprising an elongated absorbent pad (3) enclosed between a liquid-permeable casing sheet (1) facing the wearer in use of the article and a liquid-impermeable casing sheet (2), at least one of said casing sheets extending laterally beyond the absorbent pad forming an outwardly projecting, longitudinally extending edge, flexible side-flaps (5, 6) arranged at the long side edges of the absorbent pad (3) and being adapted when the article is opened and extended, to be folded around the edges of the wearer's undergarment (9) in the crotch part thereof and attached to the outside of the undergarment, uplifted liquid barrier devices (10, 11) provided on that side of the article which faces the wearer in use on both sides of the absorbent pad (3) along at least parts of the long side edges thereof between the absorbent pad and the flexible side-flaps; the improvement wherein an end portion (12, 13) of each side-flap (5, 6) is attached to the corresponding outwardly projecting edge of the casing sheet on that side thereof which, when the side-flaps are folded against the side of the article distal from the wearer in use, is facing away from the wearer, said end portion (12, 13) having an extent which is attached to said projecting edge at a distance inwardly from the outermost limit of said projecting edge corresponding to the height desired for the respective liquid barrier device (10, 11).

2. An article according to claim 1, wherein the casing (1, 2) includes a liquid-permeable sheet (1) on that side of the article which faces the wearer in use, and a liquid-impermeable sheet (2) on theft side of the article which is distal from the wearer in use, said two sheets (1, 2) extending beyond the edges of the absorbent pad (3) around the full periphery thereof and being mutually joined along the outwardly projecting edges (4) thereof, such that the absorbent pad (3) is enclosed between the sheets (1, 2); one end of respective flexible side-flaps (5, 6) being secured in the outwardly projecting casing edge (4) on the side of the article that is distal from the wearer in use, and the uplifted liquid barrier devices (10, 11) being formed by the outwardly projecting casing edge (4), at least within those regions of said edge to which the side-flaps (5, 6) are secured.

3. An article according to claim 1, wherein the uplifted liquid barrier devices (10, 11) are formed by separate bands of liquid-obstructing material secured to the article casing (1, 2).

4. An article according to claim 1, wherein the liquid barrier devices (10, 11) include elastic devices (27, 28).

5. An article according to claim 1, wherein the end parts of the liquid barrier devices (10, 11) are secured to the casing material (1, 2) on that side of the absorbent pad (3) which faces towards the wearer in use, whereby the article presents liquid-obstructing pockets on both sides of the absorbent pad (3).

6. An article according to claim 1, wherein the side flaps (5, 6) are made from a vapor-permeable, breathable material.

7. An article according to claim 1, wherein the side-flaps (5, 6) include means for securing the article to an undergarment (9).

8. An article according to claim 7, wherein the means for securing the article in an undergarment (9) has the form of regions (14, 17, 18) of pressure-sensitive melt glue.

9. An article according to claim 1, wherein said liquid-permeable casing sheet (1) and said liquid-impermeable casing sheet (2) and said side-flaps (5, 6) have side edges that overlie each other, said side-flaps being attached to said liquid-impermeable casing sheet (2) over a substantial width in a direction perpendicular to said edges.

* * * * *